(12) United States Patent
Sattler (10) Patent No.: US 8,388,913 B2
(45) Date of Patent: Mar. 5, 2013

(54) REAGENT CONTAINER SYSTEM

(75) Inventor: Stephan Sattler, Starnberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 259 days.

(21) Appl. No.: 12/732,236

(22) Filed: Mar. 26, 2010

(65) Prior Publication Data

US 2010/0233036 A1    Sep. 16, 2010

Related U.S. Application Data (63) Continuation of application No. PCT/EP2008/007999, filed on Sep. 22, 2008.

(30) Foreign Application Priority Data

Sep. 28, 2007    (EP) .................................... 07019129

(51) Int. Cl.
     *G01N 33/00*      (2006.01)
(52) U.S. Cl. ....................... 422/561; 422/569
(58) Field of Classification Search .................. 422/561, 422/569
See application file for complete search history.

(56) References Cited

U.S. PATENT DOCUMENTS

| | | | |
|---|---|---|---|
| 4,925,630 | A | 5/1990 | Grunwald |
| 5,651,941 | A | 7/1997 | Stark et al. |
| 2005/0013745 | A1 | 1/2005 | Buchanan et al. |

FOREIGN PATENT DOCUMENTS

| | | |
|---|---|---|
| DE | 295 02 834 U1 | 2/1995 |
| EP | 1 538 447 A2 | 11/2004 |
| EP | 1 808 698 A1 | 7/2007 |
| WO | 2006 056792 A1 | 6/2006 |

OTHER PUBLICATIONS

Partial International Search Report, Appl. No. PCT/EP2008/007999, Nov. 14, 2008 (3 pages).
International Preliminary Report on Patentability, Appl. No. PCT/EP2008/007999, Nov. 14, 2008 (11 pages).

*Primary Examiner* — Sam P Siefke (74) *Attorney, Agent, or Firm* — Dinsmore & Shohl LLP (57) ABSTRACT

A reagent container system for a reagent analyzer, in particular an automatic reagent analyzer, is disclosed. The system includes a first reagent container cassette provided with a first set of openings each being capable of containing a reagent therein, and a second reagent container cassette provided with a second set of openings each being capable of containing a reagent therein. The system provides the first and second reagent container cassettes at least in a storage configuration in which the container cassettes are joined together such that a longitudinal side of the first reagent container cassette is facing a longitudinal side of the second reagent container cassette. Wherein, by relative displacement, the first and second reagent container cassettes are displaceable between the storage configuration and a use configuration in which a transverse side of the first reagent container cassette is facing a transverse side of the second reagent container cassette.

20 Claims, 8 Drawing Sheets

REAGENT CONTAINER SYSTEM

CROSS REFERENCE TO RELATED APPLICATIONS

This application is a continuation of International Application No. PCT/EP2008/007999 filed Sep. 22, 2008, which claims priority to EP Application No. 07019129.1, filed Sep. 28, 2007.

TECHNICAL FIELD

Embodiments of the present invention relate to a reagent container system for a reagent analyzer, in particular an automatic reagent analyzer.

BACKGROUND

Such reagent container systems are used to make different reagents available for a usually automatic analysis in a reagent container system. In this area, systems have established themselves in the form of cassettes which feature one or more openings for receiving the reagents to be analyzed. Such well-known cassette systems may be found, for example, in the documents EP 1 808 698 A1, and EP 1 452 869 A2.

The reagent container systems should be easy to handle in respect of both being filled with reagents to be analyzed and the subsequent analysis of the reagents in the reagent analyzer for the user and also mechanically by the reagent analyzer. Furthermore, the various steps involved in filling the containers with reagents and removing the reagents from the containers must be able to be performed with a high degree of safety and time efficiency.

A reagent container system is known from the document US 2005/0142040 whereby individual sub containers can be disconnectably joined to one another so that a linear arrangement can be created of several sub containers. The several sub containers are connected to one another, disconnectably, with the help of plug-in connectors on the sides. Another embodiment sees a closure element which is put over two adjacent sub containers in order to connect them.

SUMMARY

In one embodiment, a reagent container system for use in a reagent analyzer is disclosed which comprises a first reagent container cassette provided with a first set of openings each being capable of containing a reagent therein, and a second reagent container cassette provided with a second set of openings each being capable of containing a reagent therein. A joining means is configured to join the first and second reagent container cassettes at least in a storage configuration. In the storage configuration the first and second reagent container cassettes are joined together such that a longitudinal side of the first reagent container cassette faces a longitudinal side of the second reagent container cassette. Wherein by relative displacement the first and second reagent container cassettes are displaceable between the storage configuration and a use configuration in which a transverse side of the first reagent container cassette faces a transverse side of the second reagent container cassette, and wherein at least one of the first and second set of openings is defined by one or more recesses provided in the material of the first and second reagent container cassettes, respectively.

In another embodiment, a reagent container system for use in a reagent analyzer is disclosed which comprises a first reagent container cassette provided with recesses defining a first set of openings and each being capable of containing a reagent therein, and a second reagent container cassette provided with recesses defining a second set of openings and each being capable of containing a reagent therein. The first and second reagent container cassettes are joined detachably and provide both a storage configuration, in which a longitudinal side of the first reagent container cassette contacts a longitudinal side of the second reagent container cassette, and a use configuration, in which a transverse side of the first reagent container cassette contacts a transverse side of the second reagent container cassette. A securing means secures the first and second reagent container cassettes in the use configuration, and a further securing means secures the first and second reagent container cassettes in the storage configuration.

BRIEF DESCRIPTION OF THE DRAWINGS

In the following, various embodiments of invention will be described in further detail, by way of example, with reference made to the figures. The figures show.

DETAILED DESCRIPTION

Embodiments of the present invention provide a reagent container system for use in a reagent analyzer with improved handling properties.

According to an embodiment of the invention, a reagent container system for use in a reagent analyzer is provided, the reagent container system comprising: a first reagent container cassette provided with a first set of openings each being capable of containing a reagent therein, a second reagent container cassette provided with a second set of openings each being capable of containing a reagent therein, and joining means configured to join the first and second reagent container cassettes at least in a storage configuration, where in the storage configuration the first and second reagent container cassettes are joined together and a longitudinal side of the first reagent container cassette is facing a longitudinal side of the second reagent container cassette, wherein by relative displacement the first and second reagent container cassettes are displaceable between the storage configuration and a use configuration, where a transverse side of the first reagent container cassette is facing a transverse side of the second reagent container cassette in the use configuration.

With the help of the invention, the possibility is created to put the reagent container system in a particular configuration after each stage of use, which supports and facilitates the respective process step. It is of benefit when filling or emptying the reagents into/out of the reagent container cassettes, to have as many of the reagent receiving openings next to one another as possible. For the storage and transport of the reagent container system, as compact an arrangement of the reagent container cassettes as possible is desired. This user's desire is especially served in the reagent container system at hand. In the storage configuration, the reagent container cassettes are connected longitudinally. In this way, the most compact arrangement possible of the reagent container cassettes is achieved. The joining means ensure that the reagent container cassettes are connected, at least in the storage configuration in such a way that the reagent container cassettes are stored together and as a single system. In the use configuration, the reagent container cassettes are arranged together such that the transverse sides are located next to one another. In this way, as many openings as possible can be placed adjacent to one another. The many openings can be filled all together in a single filling procedural step. In addition, in the use configuration carry over effects which often occur when openings are arranged one behind the other can be avoided, since the many openings are arranged side by side. Of course, the reagent container system may be used for different purposes by a user in either the use configuration or the storage configuration. For example, the reagent container system is preferably be filled with the reagent in the use configuration which, therefore, may also be referred to a filling configuration. The terms "use configuration" and "storage configuration", respectively, are rather defined by a certain arrangement of the reagent container cassettes.

The reagent container system allows reagents to be made available for analysis. The term reagent as used here refers to any kind of liquid which shall be made available for an analysis by means of the container system. For example, such reagent can even be a patient sample of a bodily liquid.

In a preferred embodiment, the first and second reagent container cassettes are disconnectably joined in the storage configuration. The disconnectable connection between the first and second reagent container cassettes makes it possible in one embodiment for the container cassettes to be disconnected from one another and brought into the use configuration by hand.

According a further preferred embodiment, the longitudinal side of the first reagent container cassette is in contact with the longitudinal side of the second reagent container cassette in the storage configuration. By means of contact between the longitudinal sides of the reagent container cassettes, a particularly stable construction of the reagent container system is created in the storage configuration. The longitudinal sides rest on one another.

In still a further preferred embodiment, the transverse side of the first reagent container cassette is in contact with the transverse side of the second reagent container cassette in the use configuration. In turn, the mechanical stability of the arrangement of the reagent container cassettes in the respective configuration is supported.

According to a preferred embodiment, the joining means are configured to provide a connection between the first and second reagent container cassettes in the use configuration. In this embodiment, the first and second reagent container cassettes are connected with one another in both the storage configuration and the use configuration. This enables a defined and reproducible positioning of the reagent container cassettes to in relation to one another in the various configurations.

In a preferred embodiment, the joining is provided as a disconnectable connection. For particular usage instances, it can be of benefit for the reagent container cassettes to be disconnectably joined to each other in the use configuration so that the reagent container cassettes can be separated from one another if necessary and later reconnected.

According to a further preferred embodiment, the connection is provided in a corner section, where in the corner section a corner edge of the first reagent container cassette and a corner edge of the second container cassette are facing each other.

In this embodiment, a connection can be made between the corner edges in sections or continuously. In one embodiment, the reagent container cassettes can be swiveled in relation to one another around a swivel axis along the corner connection.

In still a further preferred embodiment, the joining means comprise at least one of an articulation and a swivel-mounting. The articulation or the swivel mounting can be used to form the joined connection. As a means of forming the respective connection, for instance a bending element that joins the reagent container cassettes together for example in the form of a thin disc or film hinge could be used. However, an adhesive strip may also be used to form the swivel mounting. An elastic connection could be created, for example, using an elastomer material.

According to still a further embodiment, the joining means comprise connecting means on at least one of the longitudinal sides of the first reagent container cassette and the longitudinal sides of the second reagent container cassette. The remaining connecting means can be used to improve the mechanical stability of the arrangement of reagent container cassettes in the storage configuration. They serve to fix mutually the adjacent longitudinal sides of the reagent container cassettes. The additional fixing means can be formed using, for example, an adhesive such as a hot-melt adhesive. Double-sided adhesive tape can also be used in order to connect securely the longitudinal sides to one another in the storage configuration. As an alternative or in addition to this, the first and second reagent container cassettes could be surrounded by a securing means such as a film tube which, in particular, can be made of shrink film.

In a preferred embodiment, securing means are provided, the securing means configured to secure relative arrangement of the first and second reagent container cassettes in the use configuration. With the help of the securing means, the reagent container cassettes are held in the desired relative position in respect to one another in the use configuration. The reagent container cassettes are thus fixed in their relative positions in respect to one another.

In a further preferred embodiment, the securing means comprise at least one securing element selected from the following group of securing elements: an adhesive element, a snap element, and a plug-in element. A simple measure to secure the reagent container cassettes in the use configuration is the use of an adhesive element, which is formed with an adhesive strip with which the reagent container cassettes can be connected if necessary. Such adhesive connection means can be formed and opened again several times. As an alternative or in addition, a snap element can be made which can be snapped into place in the use configuration and then released in order to release the reagent container cassettes from the use configuration. Such a snap element can be formed by a projection on one of the reagent container cassettes and a catch on the other that hook into one another in the use configuration whereby a disconnectable connection is created. In a further embodiment, which can be an alternative or addition to the securing means described above, a recess is contained in each reagent container cassette in which a plug-in element can be inserted, disconnectably. An interlocking means can be created in addition or as an alternative with the help of a clip-on element in the shape of spectacles which when affixed goes around the necks of the containers in the reagent container cassettes.

In still a further preferred embodiment, further securing means are provided, the further securing means configured to secure relative arrangement of the first and second reagent container cassettes in the storage configuration. Through the further securing means, the relative position of the reagent container cassettes in relation to one another is secured in the storage configuration.

According to an embodiment, the further securing means comprise at least one further securing element selected from the following group of further securing elements: a further adhesive element, a further snap element, a further plug-in element, a cover element, and a foot element. The further adhesive element, the further snap element and the further plug-in element can be formed in a similar way as described above for the securing means. Naturally, the elements of the further securing means are then attached to the reagent container system in suitable positions such that further securing means can still be accessed in the storage configuration. As an alternative or in addition, a cover element can be used with several apertures, which the container openings of the reagent container cassettes fit into when the cover element is put on. The cover element fits around the reagent container cassettes from the side and thus secures their relative position to one another. In addition or as an alternative to this, a foot element can be used which the reagent container cassettes arranged in the storage configuration can be positioned. In turn, the foot element fits around the reagent container cassettes from the side.

In a preferred embodiment, at least one of the first and second set of openings is implemented by one or more recesses provided in the first and second reagent container cassettes, respectively. In this embodiment, recesses are present in the material of the reagent container cassettes for the purpose of receiving the reagents to be analyzed. The material of the reagent container cassettes can be in part transparent so that the fill level in the recesses is visible from the outside. Such transparent wall sections can be preferably on the longitudinal sides which face one another in the storage configuration. The recesses are then only visible through these sections in the use configuration.

In a further preferred embodiment, at least one of the first and second set of openings is implemented by one or more sub containers provided in the first and second reagent container cassettes, respectively. In this embodiment, there are one or more sub containers which are inserted into the respective openings in one or both reagent container cassettes. Such sub containers can be glass or plastic bottles. On the longitudinal sides which face each other in the storage configuration, the wall sections of the reagent container cassettes could be broken partially or completely through in order to view the sub containers. In this way, the fill level of the sub containers is once more visible. As an alternative or in addition, the possibility could be created whereby the sub containers could be placed in or removed from the reagent container cassettes through the perforated wall sections.

In still a further preferred embodiment, at least one of the first and second sets of openings is provided as a linear arrangement of openings. Thus, openings are arranged, for example, in a single line.

In a further embodiment, a distinguishing mark is provided on at least one of the first and second reagent container cassettes. The distinguishing marks can be, for example, RFID (Radio Frequency Identification) chips or an adhesive label that can be, where required, machine readable.

According to a preferred embodiment, the distinguishing mark is provided on at least one of the longitudinal side of the first reagent container cassette and the longitudinal side of the second reagent container cassette.

In still a further preferred embodiment, the distinguishing mark is covered in the storage configuration.

Referring to FIGS. 1 to 18, preferred embodiments of a reagent container system are described. The same reference numerals are used for the same features.

Figure 1:
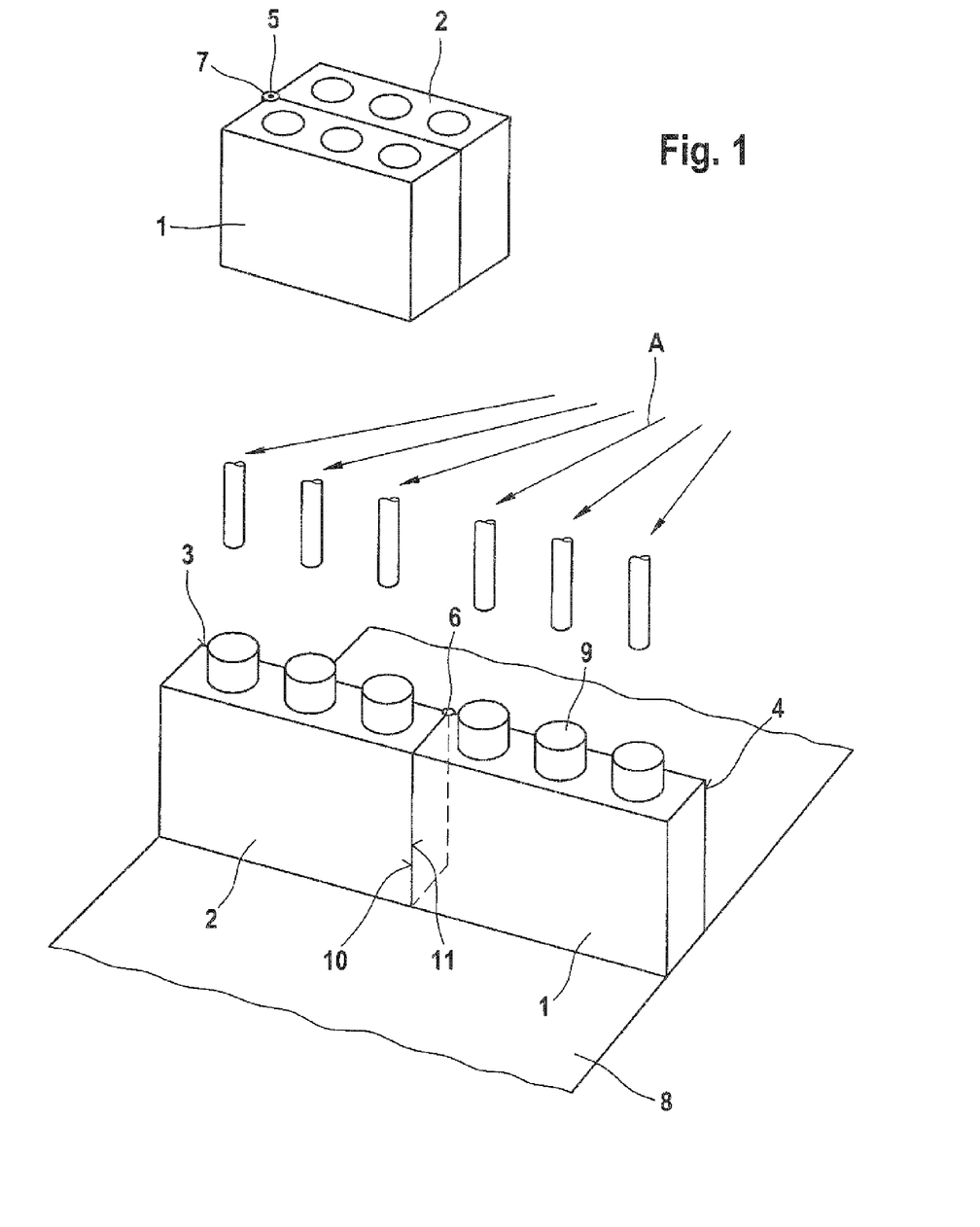
FIG. 1 is a schematic representation of a reagent container system comprising a first reagent container cassette and a second reagent container cassette in a storage configuration and a use configuration.

FIG. 1 shows a schematic representation of a reagent container system comprising a first reagent container cassette 1 and a second reagent container cassette 2 in a storage configuration and a use configuration.

The reagent container system is first provided, as in upper part of FIG. 1, in the storage configuration in which longitudinal sides 3, 4 of the first reagent container cassette 1 and the second reagent container cassette 2 are arranged adjacent to one another and touching. Once opened, the reagent container system can be released from the storage configuration and brought into the use configuration shown in the lower part of FIG. 1. This is achieved by swiveling the second reagent container cassette 2 about a swiveling axis 5 which in turn runs along an edge 6. A film hinge 7 is located at the edge 6. The storage configuration can also be called the closed/folded configuration whereas the use configuration is an unfolded/opened configuration of the reagent container cassettes 1, 2.

In the use configuration, the reagent container system can be filled with desired reagents, shown with arrow A in FIG. 1. For this, the reagent container system is on a conveyor belt 8 which serves to transport several reagent container systems past a suitable filling apparatus. A linear arrangement of openings 9 is provided by arranging transverse sides 10, 11 of the first and second reagent container cassettes 1, 2 facing one another.

Figure 2:
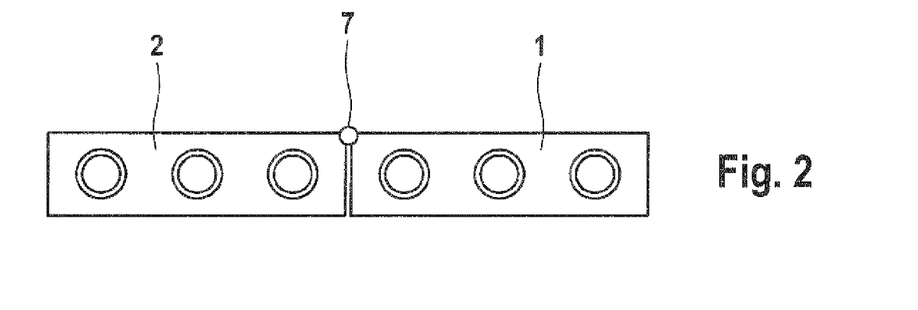
FIG. 2 is a schematic representation of a reagent container system in a use configuration, wherein a first reagent container cassette and a second reagent container cassette are joined by a film hinge.

FIG. 2 shows a schematic representation of the reagent container system in FIG. 1, wherein the first reagent container cassette 1 and the second reagent container cassette 2 are joined by the film hinge 7. The reagent container system is shown in a top view.

Figure 3:
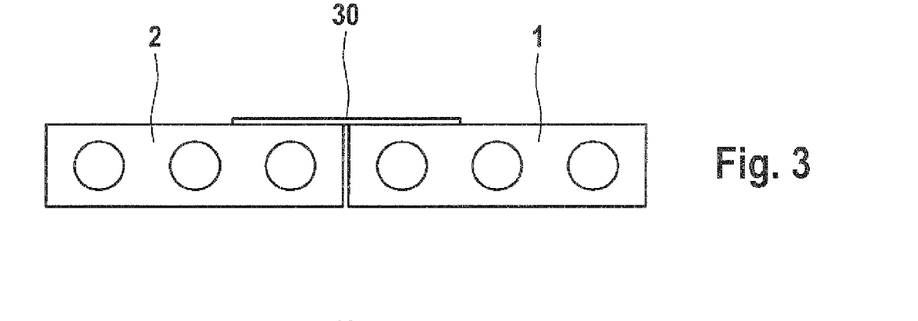
FIG. 3 is a schematic representation of a reagent container system in a use configuration, wherein a first reagent container cassette and a second reagent container cassette are joined by an adhesive element.

FIG. 3 shows a schematic representation of a reagent container system in a top view, wherein a first reagent container cassette 1 and a second reagent container cassette 2 are joined by an adhesive strip 30.

Figure 4:
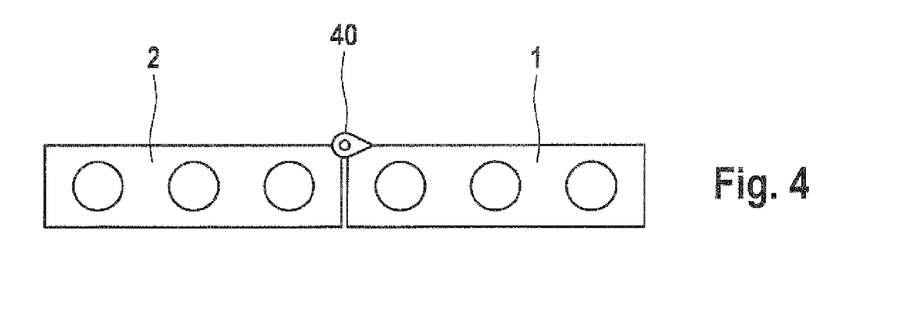
FIG. 4 is a schematic representation of a reagent container system in a use configuration, wherein a first reagent container cassette and a second reagent container cassette are joined by an articulation.

FIG. 4 shows a schematic representation of a reagent container system in a top view, wherein a first reagent container cassette 1 and a second reagent container cassette 2 are joined by an articulation 40.

Figure 5:
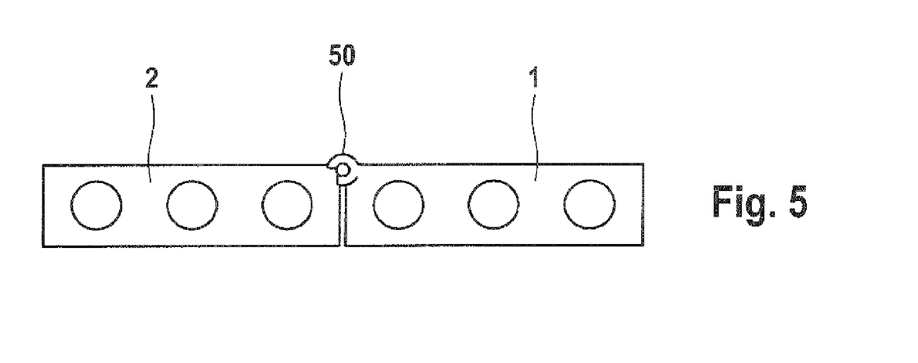
FIG. 5 is a schematic representation of a reagent container system in a use configuration, wherein a first reagent container cassette and a second reagent container cassette are joined by a snap articulation.

FIG. 5 shows a schematic representation of a reagent container system in a top view, wherein a first reagent container cassette 1 and a second reagent container cassette 2 are joined by snap articulation 50.

Figure 6:
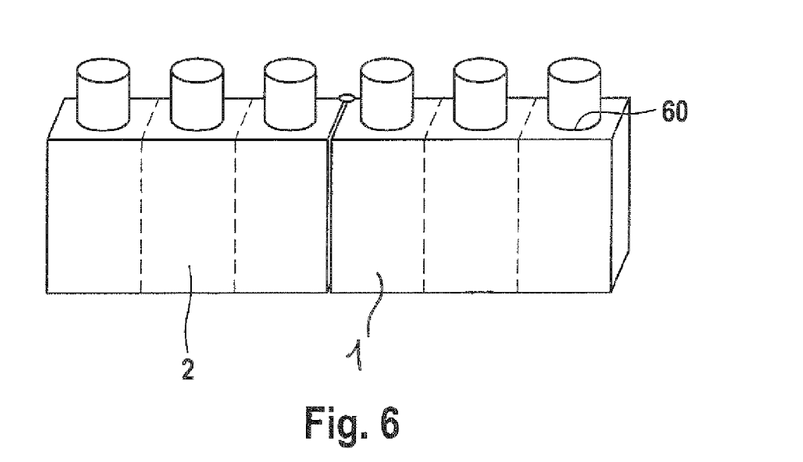
FIG. 6 is a schematic representation of a reagent container system in a use configuration, wherein a set of openings is implemented by a plurality of recesses.
Figure 7:
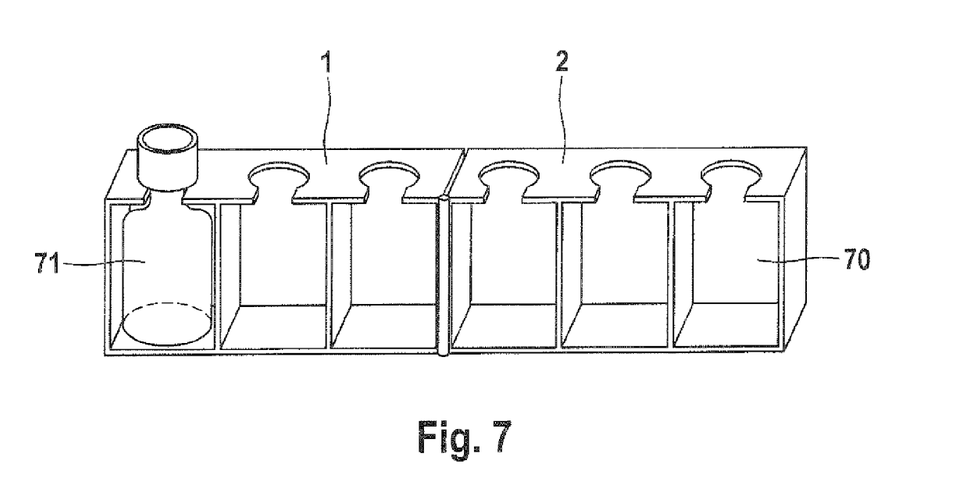
FIG. 7 is a schematic representation of a reagent container system in a use configuration, wherein a set of openings is implemented by a plurality of sub containers.

FIG. 6 shows a schematic representation of a reagent container system in a use configuration, wherein a set of openings is implemented by a plurality of recesses 60. In this embodiment, the recesses 60 are made in the material of the two reagent container cassettes 1, 2 itself. Such recesses 60 can be manufactured, with the help of the production of the reagent container system, as injection molded parts FIG. 7 shows a schematic representation of a reagent container system in a use configuration, wherein a set of openings is implemented by a plurality of sub containers. In this embodiment, spaces 70 in the first reagent container cassette 1 and the second reagent container cassette 2 are depicted in which the respective sub containers 71 can be loosely or securely placed. The sub containers 71 are made of, for example, plastic or glass and usually take the form of small bottles.

Figure 8:
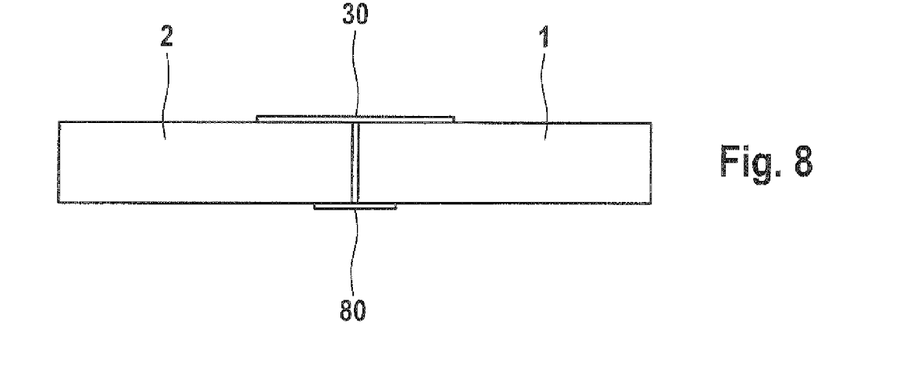
FIG. 8 is a schematic representation of a reagent container system in a use configuration, wherein a first reagent container cassette and a second reagent container cassette are fixed in a use configuration by an adhesive element.

FIG. 8 shows a schematic representation of a reagent container system, wherein a first reagent container cassette 1 and a second reagent container cassette 2 are fixed in a used configuration by an adhesive element such as e.g., an adhesive strip 80. For additional securing of the relative arrangement of the first and second reagent container cassettes 1, 2 in the use configuration shown, the adhesive strip 80 is attached.

Figure 9:
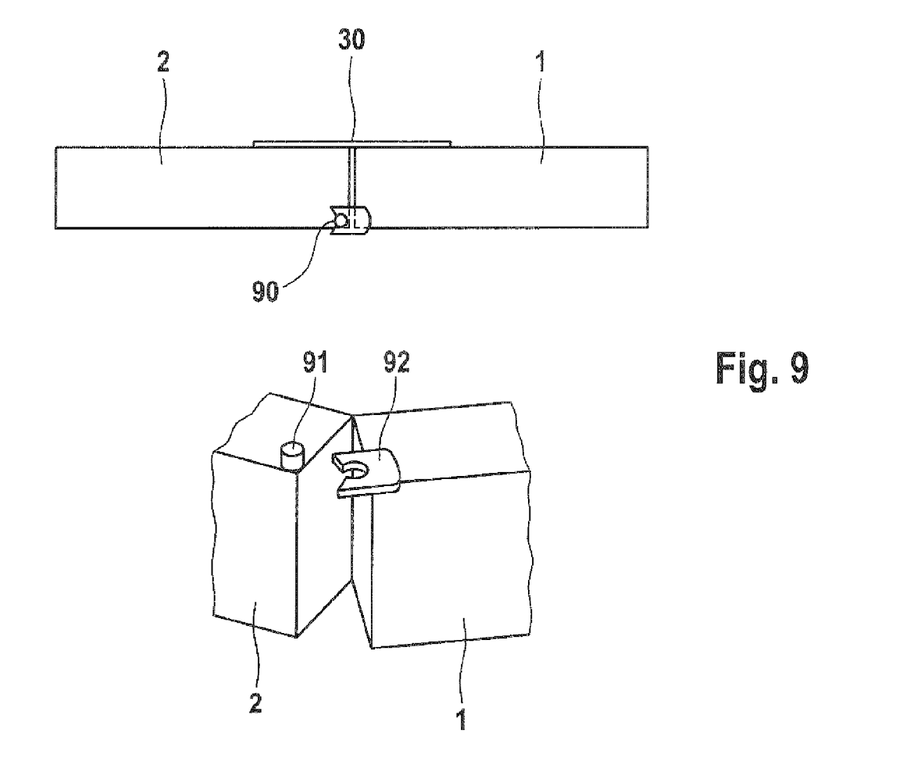
FIG. 9 is a schematic representation of a reagent container system in a use configuration, wherein a first reagent container cassette and a second reagent container cassette are fixed in a use configuration by a snap element.

FIG. 9 shows a schematic representation of a reagent container system, wherein a first reagent container cassette 1 and a second reagent container cassette 2 are fixed in a use configuration by a snap element 90. In the closed state, a projection 91 is at least partially enclosed by the open catch 92.

Figure 10:
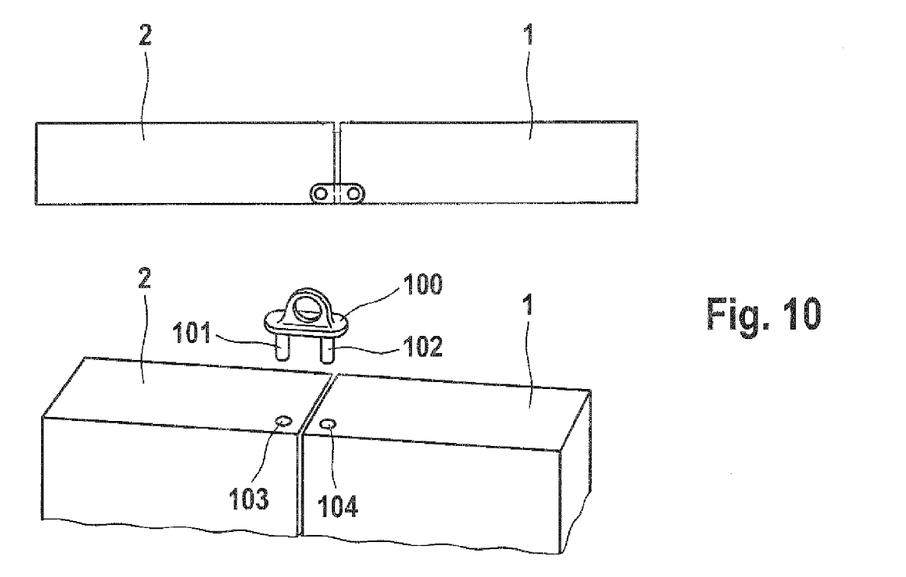
FIG. 10 is a schematic representation of a reagent container system, wherein a first reagent container cassette and a second reagent container cassette are fixed in a use configuration by a plug-in element.

FIG. 10 shows a schematic representation of a reagent container system, wherein a first reagent container cassette 1 and a second reagent container cassette 2 are fixed in a use configuration by a plug-in element 100. The plug-in element 100 has two projections 101, 102 which slot into the allocated recesses 103, 104 in order to secure the first and second reagent container cassettes 1, 2 in the use configuration.

Figure 11:
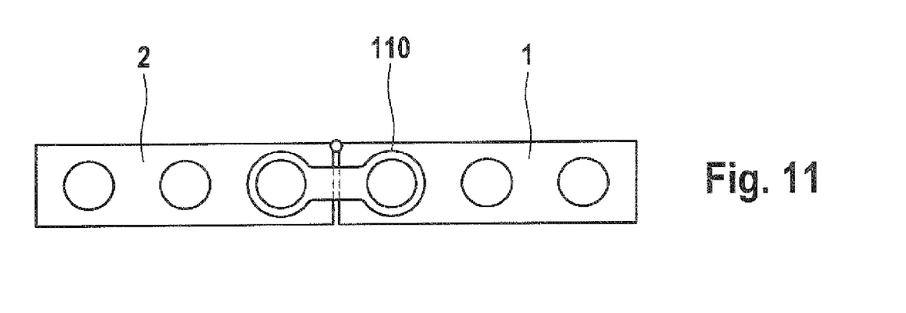
FIG. 11 is a schematic representation of a reagent container system, wherein a first reagent container cassette and a second reagent container cassette are fixed in a use configuration by a joining member.

FIG. 11 shows a schematic representation of a reagent container system, wherein a first reagent container cassette 1 and a second reagent container cassette 2 are fixed in a use configuration by a joining member 110. As shown, the joining is provided in a corner portion, where in the corner portion a corner edge of the first reagent container cassette 1 and a corner edge of the second reagent container cassette 2 are facing each other.

Figure 12:
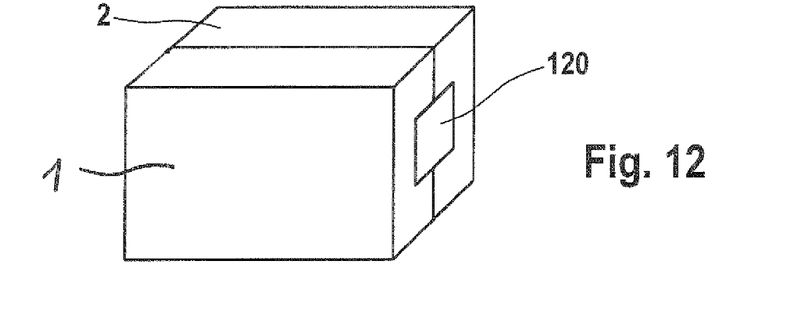
FIG. 12 is a schematic representation of a reagent container system comprising a first reagent container cassette and a second reagent container cassette in a storage configuration, wherein the reagent container cassettes are secured by an adhesive element.

FIG. 12 shows a schematic representation of a reagent container system comprising a first reagent container cassette 1 and a second reagent container cassette 2 in a storage configuration, wherein the reagent container cassettes 1, 2 are secured by an adhesive element 120.

Figure 13:
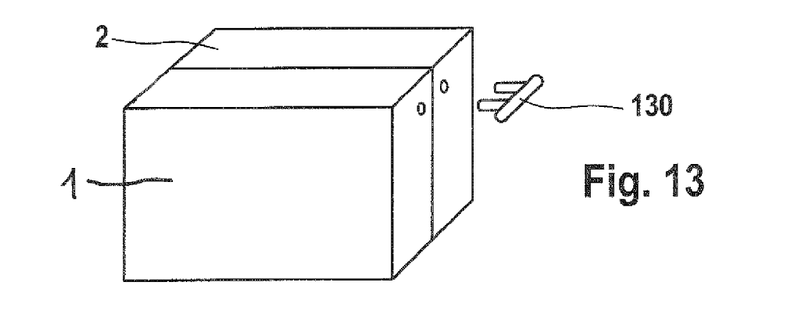
FIG. 13 is a schematic representation of a reagent container system comprising a first reagent container cassette and a second reagent container cassette in a storage configuration, wherein the reagent container cassettes are secured by a plug-in member.

FIG. 13 shows a schematic representation of a reagent container system comprising a first reagent container cassette 1 and a second reagent container cassette 2 in a storage configuration, wherein the reagent container cassettes 1, 2 are secured by a plug-in member 130.

Figure 14:
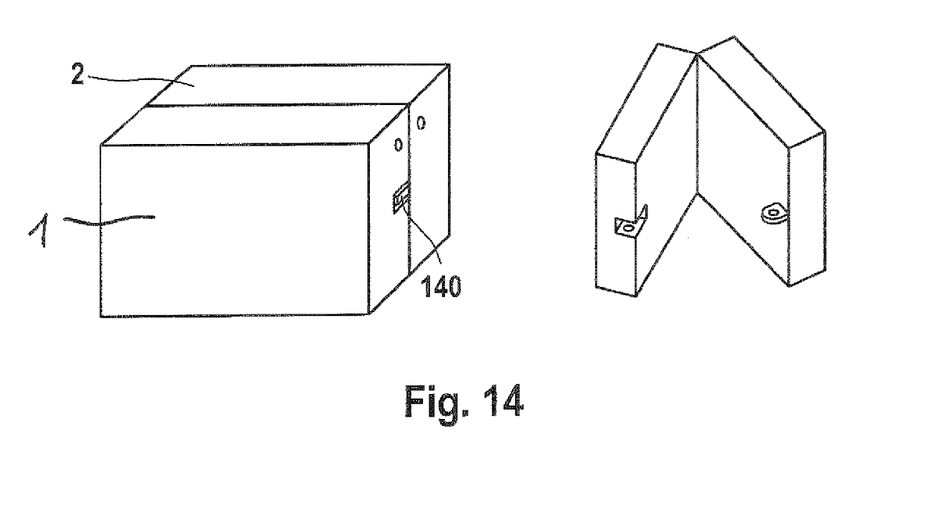
FIG. 14 is a schematic representation of a reagent container system comprising a first reagent container cassette and a second reagent container cassette in a storage configuration, wherein the reagent container cassettes are secured by a snap element.

FIG. 14 shows a schematic representation of a reagent container system comprising a first reagent container cassette 1 and a second reagent container cassette 2 in a storage configuration, wherein the reagent container cassettes 1, 2 are secured by a snap element 140.

Figure 15:
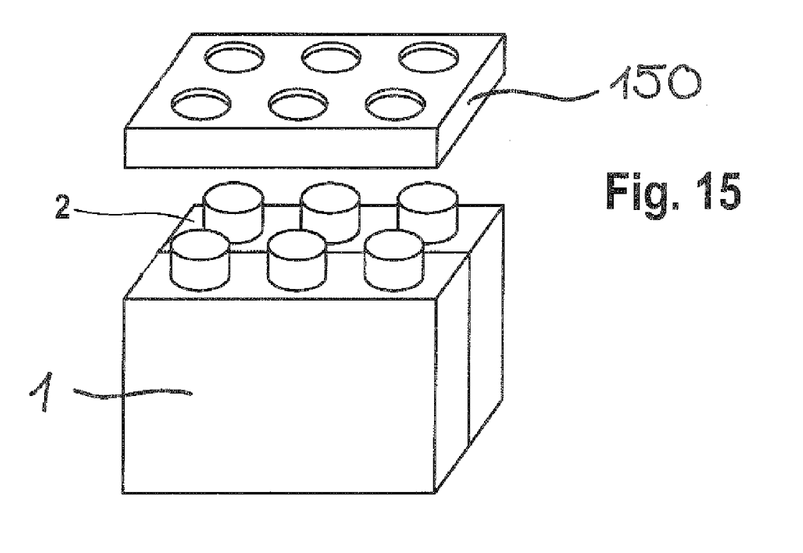
FIG. 15 is a schematic representation of a reagent container system comprising a first reagent container cassette and a second reagent container cassette in a storage configuration, wherein the reagent container cassettes are secured by a cover element.

FIG. 15 shows a schematic representation of a reagent container system comprising a first reagent container cassette 1 and a second reagent container cassette 2 in a storage configuration, wherein the reagent container cassettes 1, 2 are secured by a cover element 150.

Figure 16:
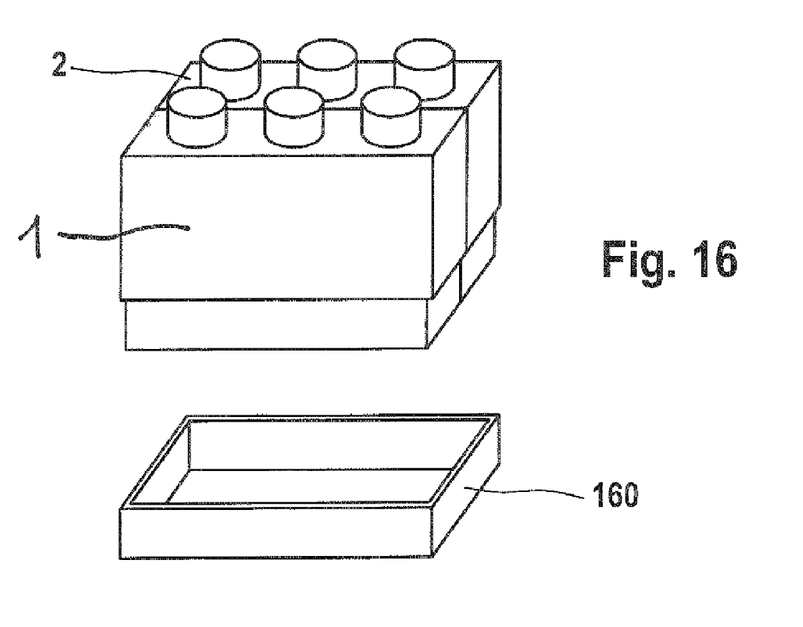
FIG. 16 is a schematic representation of a reagent container system comprising a first reagent container cassette and a second reagent container cassette in a storage configuration, wherein the reagent container cassettes are secured by a foot element.

FIG. 16 shows a schematic representation of a reagent container system comprising a first reagent container cassette 1 and a second reagent container cassette 2 in a storage configuration, wherein the reagent container cassettes 1, 2 are secured by a foot element 160. The two reagent container cassettes 1, 2 are positioned in the foot element 160 and thus secured in the storage configuration.

Figure 17:
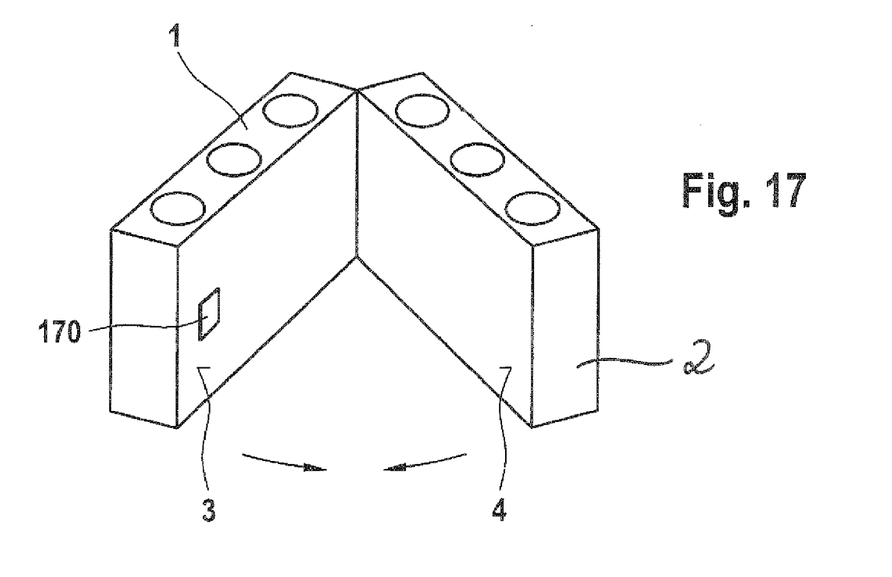
FIG. 17 is a schematic representation of a reagent container system comprising a first reagent container cassette and a second reagent container cassette, wherein further securing means are provided on longitudinal sides facing each other in the storage configuration.

FIG. 17 shows a schematic representation of a reagent container system comprising a first reagent container cassette 1 and a second reagent container cassette 2, wherein further securing means 170 are provided on the longitudinal sides 3, 4 facing each other in the storage configuration. The further securing means 170 are provided as an adhesive material. In other embodiments, a plug-in or a snap connection may be provided.

Figure 18:
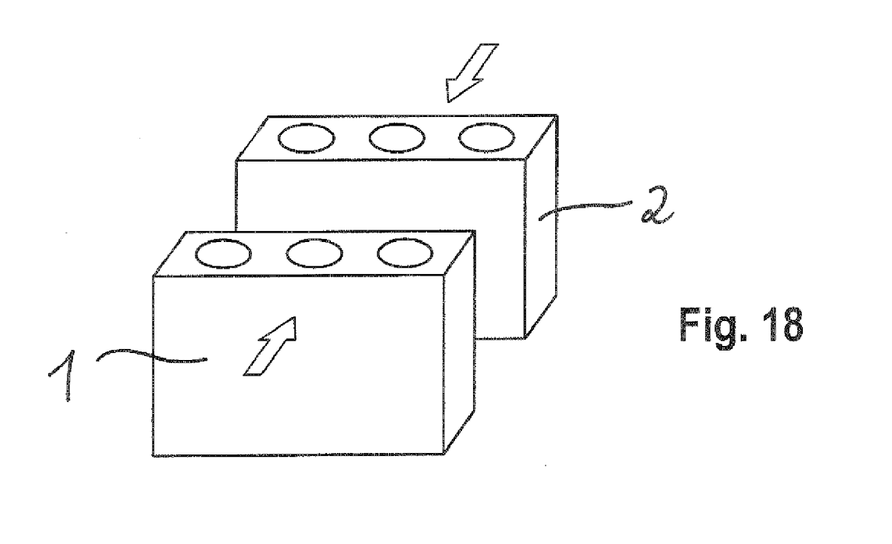
FIG. 18 is a schematic representation of a reagent container system comprising a first reagent container cassette and a second reagent container cassette which are disconnectably joined in a storage configuration after the reagent container cassettes have been filled in a use configuration where the reagent container cassettes are separated from each other.

FIG. 18 shows a schematic representation of a reagent container system comprising a first reagent container cassette 1 and a second reagent container cassette 2 which are disconnectably joined in the storage configuration after the reagent container cassettes 1, 2 have been filled in the use configuration where the reagent container cassettes 1, 2 are separated from each other.

The different embodiments of the reagent container system have been described using embodiments where two reagent container cassettes are depicted, namely the first reagent container cassette 1 and the second reagent container cassette 2. However, it can be provided for that more than two reagent container cassettes can be combined in a similar way in the reagent container system whereby these can be arranged such that adjacent reagent container cassettes have transverse sides facing in the use configuration and longitudinal sides facing in the storage configuration. Both configurations constitute a closed position and an open position which may also referred to as a fold and an unfold position (configuration), respectively. For example, several reagent container cassettes can be connected to one another using the connection methods described above so that they are in accordion like formation.

The features disclosed in at least one of the specification, the claims, and the figures may be material for the realization of the invention in its various embodiments, taken in isolation or in various combinations thereof.

What is claimed is:

1. A reagent container system for use in a reagent analyzer comprising:
   a first reagent container cassette provided with a first set of openings each being capable of containing a different reagent therein, wherein each different reagent is in direct contact with the material of the first reagent container cassette;
   a second reagent container cassette provided with a second set of openings each being capable of containing a different reagent therein, wherein each different reagent is in direct contact with the material of the second reagent container cassette; and
   a joining means configured to join the first and second reagent container cassettes at least in a storage configuration, where in the storage configuration the first and second reagent container cassettes are joined together such that a longitudinal side of the first reagent container cassette faces a longitudinal side of the second reagent container cassette,
   wherein by relative displacement the first and second reagent container cassettes are displaceable between the storage configuration and a use configuration in which a transverse side of the first reagent container cassette faces a transverse side of the second reagent container cassette, and
   wherein at least one of the first and second set of openings is defined by one or more recesses provided in the material of the first and second reagent container cassettes, respectively, and
   further comprising a wall between each adjacent recess in the first reagent container and a wall between each adjacent recess in the second reagent container, each wall capable of restricting a reagent in a recess from entering another recess.

2. The reagent container system according to claim 1, wherein the first and second reagent container cassettes are disconnectably joined in the storage configuration.

3. The reagent container system according to claim 1, wherein the longitudinal side of the first reagent container cassette is in contact with the longitudinal side of the second reagent container cassette in the storage configuration.

4. The reagent container system according to claim 1, wherein the transverse side of the first reagent container cassette is in contact with the transverse side of the second reagent container cassette in the use configuration.

5. The reagent container system according to claim 1, wherein the joining means is configured to provide a joining between the first and second reagent container cassettes in the use configuration.

6. The reagent container system according to claim 5, wherein the joining means provides a disconnectable connection.

7. The reagent container system according to claim 5, wherein the joining means is provided in a corner portion, where in the corner portion a corner edge of the first reagent container cassette and a corner edge of the second reagent container cassette are facing each other.

8. The reagent container system according to claim 1, wherein the joining means comprises at least one of an articulation and a swivel-mounting.

9. The reagent container system according to claim 1, wherein the joining means comprises connecting means on at least one of the longitudinal side of the first reagent container cassette and the longitudinal side of the second reagent container cassette.

10. The reagent container system according to claim 1, further comprises a securing means which secures the relative arrangement of the first and second reagent container cassettes in the use configuration.

11. The reagent container system according to claim 10, wherein the securing means comprises at least one securing element selected from the following group of securing elements: an adhesive element, a snap element, and a plug-in element.

12. The reagent container system according to claim 1, further comprises a securing means which secures the relative arrangement of the first and second reagent container cassettes in the storage configuration.

13. The reagent container system according to claim 12, wherein the securing means comprises at least one securing element selected from the following group of securing elements: a adhesive element, a snap element, a plug-in element, a cover element, and a foot element.

14. The reagent container system according to claim 1, wherein at least one of the first and second set of openings is implemented by one or more sub-containers provided in the first and second reagent container cassettes, respectively.

15. The reagent container system according to claim 1, wherein at least one of the first and second set of openings is provided as a line arrangement of openings.

16. The reagent container system according to claim 1, wherein a distinguishing mark is provided on at least one of the first and second reagent container cassettes.

17. The reagent container system according to claim 16, wherein the distinguishing mark is provided on at least one of the longitudinal side of the first reagent container cassette and the longitudinal side of the second reagent container cassette.

18. The reagent container system according to claim 16, wherein the distinguishing mark is covered in the storage configuration.

19. A reagent container system for use in a reagent analyzer comprising:
   a first reagent container cassette provided with recesses defining a first set of openings and each being capable of containing a different reagent therein, wherein each different reagent is in direct contact with the material of the first reagent container cassette;
   a second reagent container cassette provided with recesses defining a second set of openings and each being capable of containing a different reagent therein, wherein each different reagent is in direct contact with the material of the second reagent container cassette,
   the first and second reagent container cassettes being joined detachably and providing both a storage configuration, in which a longitudinal side of the first reagent container cassette contacts a longitudinal side of the second reagent container cassette, and a use configuration, in which a transverse side of the first reagent container cassette contacts a transverse side of the second reagent container cassette;
   a securing means which secures the first and second reagent container cassettes in the use configuration;

a further securing means which secures the first and second reagent container cassettes in the storage configuration:, a wall between each adjacent recess in the first reagent container capable of restricting a reagent in a recess from entering another recess; and a wall between each adjacent recess in the second reagent container capable of restricting a reagent in a recess from entering another recess.

20. The reagent container system according to claim 19, wherein the securing means comprises at least one securing element selected from the following group of securing elements: an adhesive element, a snap element, and a plug-in element; and wherein the further securing means comprises at least one further securing element selected from the following group of further securing elements: a further adhesive element, a further snap element, a further plug-in element, a cover element, and a foot element.

* * * * *

UNITED STATES PATENT AND TRADEMARK OFFICE
CERTIFICATE OF CORRECTION

PATENT NO. : 8,388,913 B2
APPLICATION NO. : 12/732236
DATED : March 5, 2013
INVENTOR(S) : Stephan Sattler It is certified that error appears in the above-identified patent and that said Letters Patent is hereby corrected as shown below:

In the Claims

Col. 10, Claim 7, Line 3, "where in" should read --wherein--;

Col. 10, Claim 13, Line 29, "a adhesive element" should read --an adhesive element--; and Col. 11, Claim 19, Line 2, "configuration:," should read --configuration;--.

Signed and Sealed this
Fourth Day of June, 2013

Teresa Stanek Rea
*Acting Director of the United States Patent and Trademark Office*